United States Patent
Ruan et al.

(10) Patent No.: US 8,971,489 B2
(45) Date of Patent: Mar. 3, 2015

(54) METHOD AND SYSTEM FOR REAL-TIME DMLC-BASED TARGET TRACKING WITH OPTIMAL MOTION COMPENSATING LEAF ADAPTATION

(75) Inventors: Dan Ruan, Los Angeles, CA (US); Paul J. Keall, Greenwich (AU); Amit Sawant, Richardson, TX (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 335 days.

(21) Appl. No.: 13/261,121

(22) PCT Filed: Jul. 9, 2010

(86) PCT No.: PCT/US2010/001944
§ 371 (c)(1),
(2), (4) Date: Jan. 5, 2012

(87) PCT Pub. No.: WO2011/005329
PCT Pub. Date: Jan. 13, 2011

(65) Prior Publication Data
US 2012/0099704 A1  Apr. 26, 2012

Related U.S. Application Data

(60) Provisional application No. 61/270,666, filed on Jul. 9, 2009.

(51) Int. Cl.
*A61N 5/10* (2006.01)
*G21K 1/04* (2006.01)
*H05G 1/28* (2006.01)
*A61B 6/06* (2006.01)
*G21K 1/02* (2006.01)

(52) U.S. Cl.
CPC .............. *G21K 1/025* (2013.01); *A61N 5/1031* (2013.01); *A61N 5/1036* (2013.01); *A61N 5/1037* (2013.01);
(Continued)

(58) Field of Classification Search
CPC .............. G21K 5/00; G21K 5/04; G21K 1/00; G21K 1/02; G21K 1/04; A61N 5/00; A61N 5/10; A61N 5/103; A61N 5/1031; A61N 5/1036; A61N 5/1037; A61N 5/1038; A61N 5/1045; A61N 5/1071; A61N 5/1048; A61N 5/1049; A61N 5/1064; A61N 5/1065; A61N 5/1067; A61N 5/1075; A61N 5/01; A61B 6/00; A61B 6/06; A61B 6/405; A61B 19/00; A61B 19/20; A61B 19/50
USPC .............. 378/20, 65, 68, 69, 95, 145, 901, 2, 378/147–153, 165, 210; 600/427
See application file for complete search history.

(56) References Cited

U.S. PATENT DOCUMENTS

2005/0111621 A1*  5/2005  Riker et al. ..................... 378/65
2006/0256915 A1* 11/2006  Otto et al. ....................... 378/65
(Continued)

*Primary Examiner* — Anastasia Midkiff
(74) *Attorney, Agent, or Firm* — Lumen Patent Firm

(57) ABSTRACT

A method of multileaf collimator (MLC) leaf positioning in tracking-based adaptive radiotherapy is provided. The method includes determining a radiotherapy beam pattern by transforming a treatment beam plan into radiotherapy beam coordinates, determining a dose discrepancy between the radiotherapy beam pattern and a deliverable MLC aperture, where the dose discrepancy includes a sum of an overdose cost and an underdose cost to a treatment volume, and minimizing the dose discrepancy, where the dose discrepancy minimization provides a determined deliverable MLC aperture for the radiotherapy beam.

6 Claims, 4 Drawing Sheets

(52) U.S. Cl.
CPC ............ *A61N 5/1038* (2013.01); *A61N 5/1045* (2013.01); *A61N 5/1067* (2013.01); *G21K 1/04* (2013.01)
USPC .............................. 378/65; 378/151; 378/165

(56) References Cited

U.S. PATENT DOCUMENTS

| | | | |
|---|---|---|---|
| 2007/0041494 A1* | 2/2007 | Ruchala et al. | 378/65 |
| 2007/0041495 A1* | 2/2007 | Olivera et al. | 378/65 |
| 2007/0041497 A1* | 2/2007 | Schnarr et al. | 378/65 |
| 2007/0041499 A1* | 2/2007 | Lu et al. | 378/65 |
| 2007/0043286 A1* | 2/2007 | Lu et al. | 600/407 |
| 2007/0064871 A1* | 3/2007 | Earl et al. | 378/65 |
| 2007/0189591 A1* | 8/2007 | Lu et al. | 382/128 |
| 2007/0195930 A1* | 8/2007 | Kapatoes et al. | 378/65 |
| 2008/0159478 A1* | 7/2008 | Keall et al. | 378/65 |
| 2009/0316858 A1 | 12/2009 | Nord et al. | |
| 2010/0046713 A1 | 2/2010 | Nord et al. | |

\* cited by examiner

_US 8,971,489 B2_

METHOD AND SYSTEM FOR REAL-TIME DMLC-BASED TARGET TRACKING WITH OPTIMAL MOTION COMPENSATING LEAF ADAPTATION

CROSS-REFERENCE TO RELATED APPLICATIONS

This application is a 371 of PCT Patent Application PCT/US2010/001944 filed Jul. 9, 2010, which claims the benefit of U.S. Provisional Application 61/270,666 filed Jul. 9, 2009.

STATEMENT OF GOVERNMENT SPONSORED SUPPORT

This invention was made with Government support under contract CA093626 awarded by National Institutes of Health. The Government has certain rights in this invention.

FIELD OF THE INVENTION

The current invention relates to radiotherapy. More particularly, the invention relates to systematically adjust a multileaf collimator (MLC) to conform to the geometric and topological motion of a treatment volume encompassing the target during the course of radiotherapy.

BACKGROUND OF THE INVENTION

Radiotherapy aims to deliver an ablative dose to the tumour with minimal normal tissue exposure. However, anatomical motion during treatment results in misalignment between beam and target, compromising treatment efficacy. An ideal motion management strategy is to reposition and reshape the beam aperture in response to instantaneous motion. There exists a need to provide an optimal deliverable beam pattern. For multileaf collimator (MLC) tracking based delivery, a systematic leaf adaptation method is desired.

Given an estimate of instantaneous motion, it is desirable to transform the planning beam according to the such motion to generate an ideal aperture. However, such an ideal aperture is often undeliverable, due to physical constraints such as finite MLC leaf widths, and more importantly, the paired leaf structure.

What is needed is an optimization framework that provides a deliverable MLC configuration that is closest to the ideal aperture, where closeness is defined rigorously as the cumulative cost in terms of underdose to target and overdose to healthy tissue.

SUMMARY OF THE INVENTION

To address the shortcomings in the art, a method of multileaf collimator (MLC) leaf positioning in tracking-based adaptive radiotherapy is provided. The method includes determining a radiotherapy beam pattern by transforming a treatment beam plan into radiotherapy beam coordinates, determining a dose discrepancy between the radiotherapy beam pattern and a deliverable MLC aperture, where the dose discrepancy includes a sum of an overdose cost and an underdose cost to a treatment volume, and minimizing the dose discrepancy, where the dose discrepancy minimization provides a determined deliverable MLC aperture for the radiotherapy beam.

In one aspect of the invention, the radiotherapy beam coordinates are based on the projection of the translation, rotation and/or deformation of all or part of a radiotherapy beam pattern into the beam coordinates.

In another aspect of the invention, the overdose cost includes an integration of pixelwise overdose penalties, where the overdose penalties can be spatially variant.

In a further aspect of the invention, the underdose cost includes an integration of pixelwise underdose penalties, where the underdose penalties can be spatially variant.

In yet another aspect of the invention, at least one previously determined dose discrepancy is used when determining a next deliverable MLC aperture for the radiotherapy beam.

In a further aspect of the invention, a determination of the overdose cost and a determination of the underdose cost are based on a tissue type and a radio-sensitivity of the tissue.

DETAILED DESCRIPTION

Radiation therapy aims to deliver an ablative radiation dose to tumor targets while sparing the surrounding normal healthy tissue. While current development in radiotherapy machines enables focused radiation beams to be directed with high precision, anatomical motion during treatment causes misalignment between the external beam and the internal anatomy, compromising the treatment efficacy. Therefore, it is important to reduce the impact of motion in radiotherapy. To achieve this goal, one aspect of the current invention synchronizes the treatment with anatomical motion, broadly known as "tracking".

Figure 1:
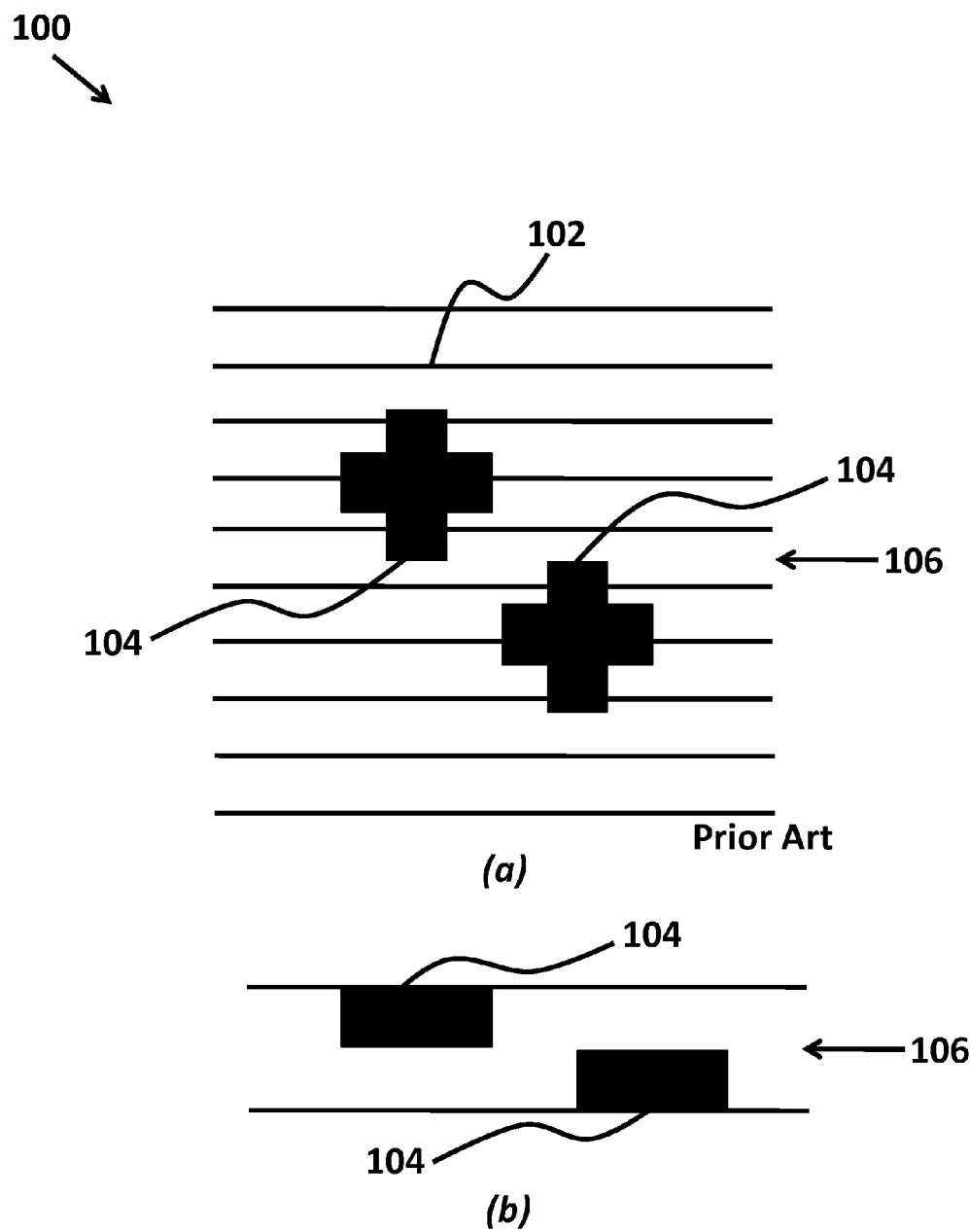
FIGS. 1a-1b show an undeliverable beam aperture.

The key idea behind tracking-based adaptive radiotherapy is to modify the treatment plan and reposition the beam to compensate for the anatomical motion. When rigid translational anatomical motion is assumed, there is a simple scheme to move the MLC to "follow" the target. When general motion is considered, however, a more sophisticated and systematic scheme is required for MLC adaptation. The most ideal situation would be performing a full-fledged re-planning in real-time. However, this is impractical due to heavy computation and the as-yet unresolved quality assurance issue. The problem of leaf arrangement for real-time intensity modulation has been studied quite intensively. The current invention applies a first order approximation to this ideal situation by adapting the MLC leaf configuration derived from a treatment plan to the instantaneous motion. The planned beam aperture is transformed with a collapsed transformation describing online motion on the beam-eye-view (BEV) plane to generate a new aperture. However, motion could transform a deliverable beam aperture into quite complex shapes that are no longer deliverable, due to paired leaf structure with finite leaf resolution. More specifically, this occurs when a single leaf track intersects with multiple open apertures. Referring now to the figures, FIGS. 1a-1b show a schematic drawing of an MLC system 100, where multiple leafs 102 are configured to provide at least one aperture 104 that is an optimization-based leaf sequencing methodology that outputs a deliverable leaf configuration that best approximates the ideal pattern. FIG.

1a shows an ideal aperture 104 is generated by translating a deliverable planned aperture by a fraction of the width of a leaf 102. The single leaf track 106 in FIG. 1a is enlarged in FIG. 1b, which intersects two open apertures 104. There exists no placement of the leaf 102 that could exactly realize this pattern. In fact, with the motion perpendicular to direction of the leaf 102 being a fraction of the width of the leaf 102, no exact placement of the leaf 102 exists for any of the leaves 102 intersecting ideal aperture 104.

Another challenge for tracking-based adaptive radiotherapy is the differential motion between tumor target and critical structures. The majority of existing studies for tracking based treatment adaptation are based on the assumption that the complete region of interest (ROI) undergoes similar motion, so the relative anatomical configuration is maintained throughout treatment. The feasibility of this assumption very much depends on the site, where it is more valid for prostate but is questionable for treating thoracic tumors, which may move towards the spinal cord with respiration. Therefore, it is desirable to have a leaf adaptation method that automatically accounts for the potential varying structural characteristics of the ROI. This property is embedded naturally in the optimization aspect of the current invention.

The current invention addresses the leaf sequencing problem described above in the presence of motion. According to one aspect, a plan aperture f and an estimated anatomical motion T are collapsed onto the BEV following the methodology described above. The ideal motion-compensated aperture is given by composing the plan aperture with the collapsed BEV motion g=f·T. According to the invention, this map is represented with a binary function over the ROI: $\Omega \to \{0,1\}$, so that $$g(x) = \begin{cases} 1 & x \in \text{transformed plan aperture opening} \\ 0 & \text{else,} \end{cases}$$

where $\underline{x}=(x, y)$ denotes the beam element location in the BEV. Since leaf sequencing is of interest to approximate the desired beam pattern g, it suffices to consider the ROI in the 2-dimensional BEV coordinate.

Without loss of generality, x-coordinate is aligned with the leaf tracking direction. Let $\Delta$ be the leaf resolution along y-direction and the complete aperture is covered by the range of N leaves, starting from y=0. The problem is restated as: finding the best N pairs of leading and trailing locations that delivers an aperture that is closest to the ideal beam pattern given by g. The leaf positions are parameterized as $\{\alpha_i^L, \alpha_i^T\}$ where the subindex i=1, 2, . . . , N indexes the leaf pair and the superscripts L and T indicate the leading and trailing leaf respectively.

Figure 2:
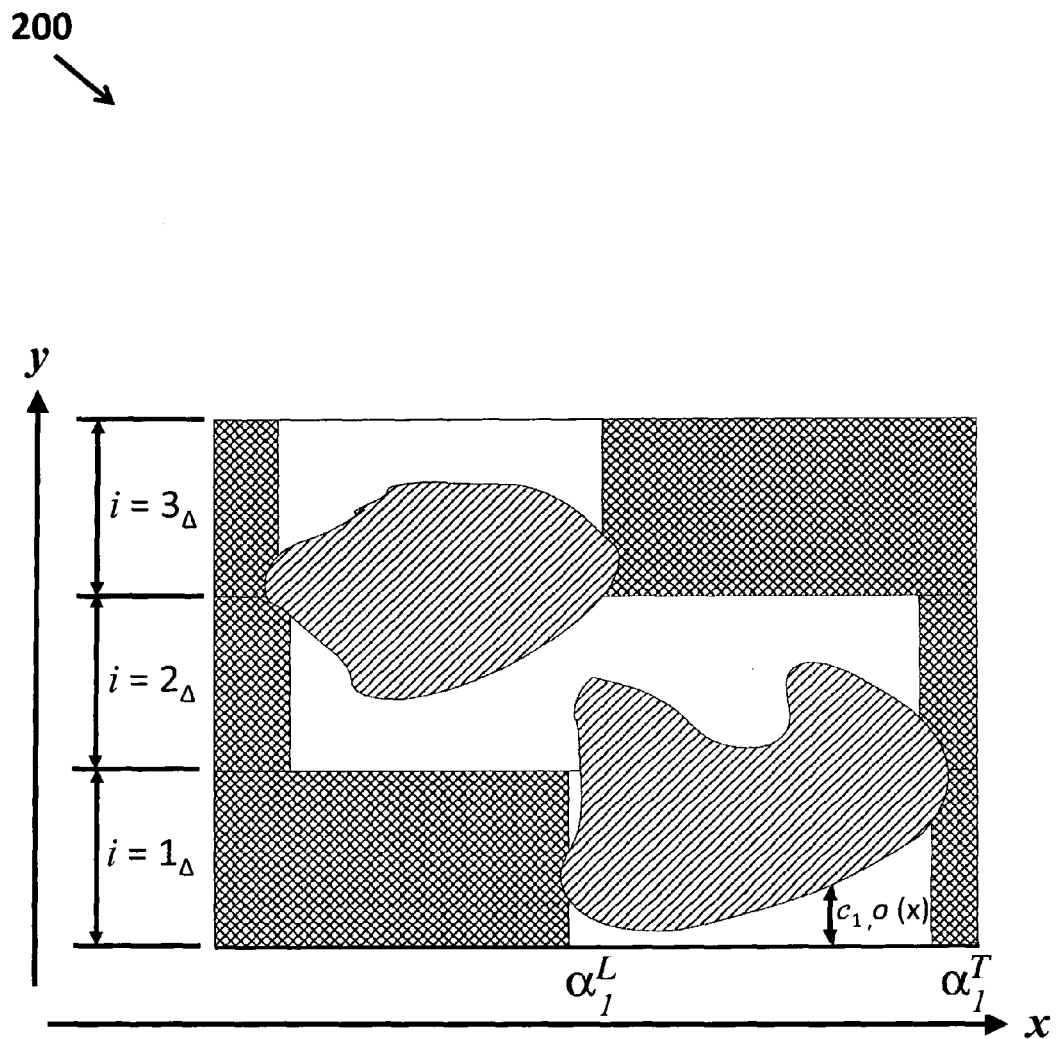
FIG. 2 shows a schematic of a leaf fitting configuration, according to the current invention.
Figure 3:
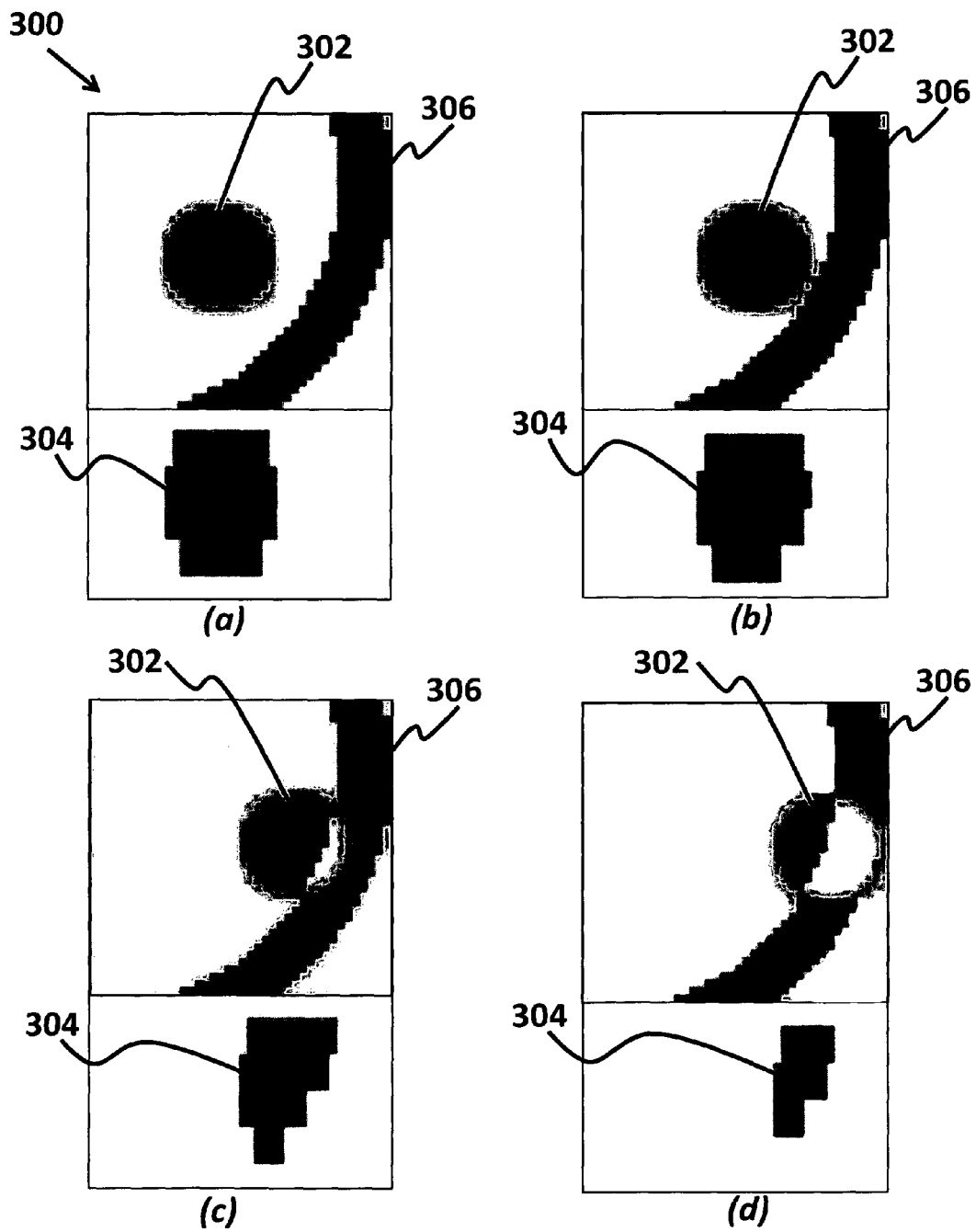
FIGS. 3a-3d show automatic leaf sequencing with the optimization method, according to the current invention.

To rigorously define an optimization objective, the "dose" discrepancy between a deliverable aperture corresponding to $\{\alpha_i^L, \alpha_i^T\}_{i}^{N}=1$ and the desired beam pattern g are qualified. Such a discrepancy is characterized as the sum of underdose and overdose cost. A pair of unitary underdose and overdose costs $\lambda u(\underline{x})$, $\lambda o(\underline{x})$ are associated with each voxel location, based on its tissue type and radio-sensitivity. If $\underline{x}$ belongs to tumor region, then the local underdose cost $\lambda u(\underline{x})$ should be high and the local overdose cost $\lambda o(\underline{x})$ should be low. Conversely, for radiosensitive healthy tissues that should be prevented from radiation, $\lambda u(\underline{x})$ should be low and $\lambda o(\underline{x})$ high. A tumor voxel desired to be irradiated ($g(\underline{x})=1$) but blocked by the delivered MLC pattern contributes an underdose cost $\lambda u(\underline{x})$ to the overall discrepancy; conversely, a healthy tissue voxel desired to be shielded ($g(\underline{x})=0$) but exposed by the delivered MLC pattern contributes an overdose cost $\lambda o(\underline{x})$ to the overall discrepancy. FIG. 2 shows a schematic of the leaf fitting setup 200.

Assume the leaf tracks are of widths $\Delta$, then the underdose cost for leaf track i is given by:

$$\Phi_{i,u} = \int_{\underline{x}: x \in [L, \alpha_i^L] \cup (\alpha_i^T, R], y \in [(i-1)\Delta, i\Delta]} \lambda_u(\underline{x}) g(\underline{x});$$

and the overdose cost reads:

$$\Phi_{i,o} = \int_{\underline{x}: x \in (\alpha_i^L, \alpha_i^T), y \in [(i-1)\Delta, i\Delta]} \lambda_o(\underline{x})(1-g(\underline{x}));$$

Where L and R indicate the left and right jaw location.

To reveal the dependence of $\Phi_{i,o}$ and $\Phi_{i,u}$ on the parameters $\{\alpha_i^L, \alpha_i^T\}$, the indicator function I is invoked:

$$I(u) = \begin{cases} 1 & u > 0; \\ 0 & \text{else.} \end{cases}$$

Then the underdose and overdose cost can be rewritten as $$\Phi_{i,u} = \int_{\underline{x}: y \in [(i-1)\Delta, i\Delta]} \lambda_u(\underline{x}) g(\underline{x}) [I(\alpha_i^L - x) + I(x - \alpha_i^T)];$$

$$\Phi_{i,o} = \int_{\underline{x}: y \in [(i-1)\Delta, i\Delta]} \lambda_o(\underline{x})(1-g(\underline{x})) I(x-\alpha_i^L)(\alpha_i^T - x).$$

The objective is to find $\{\alpha_i^L, \alpha_i^T\}$ to minimize the overall objective:

$$\Phi = \sum_i \Phi_{i,u} + \Phi_{i,o}.$$

For simplicity, the leaf velocity condition is ignored in the introduction of basic formulation, where this condition can be incorporated by imposing constraints on the optimization problem.

In the absence of any additional constraint, the summation form of the objective function enables decoupled optimization for each leaf pair, i.e., it suffices to minimize $$\Phi_i = \Phi_{i,u} + \Phi_{i,o}.$$

From here, a specific leaf track is studied and all integrations are restricted to this range. Note that $$\Phi_{i,u} = \int_{\underline{x}: y \in [(i-1)\Delta, i\Delta]} \lambda_u(\underline{x}) g(\underline{x}) [I(\alpha_i^L - x) + I(x - \alpha_i^T)];$$

$$\Phi_{i,o} = \int_{\underline{x}: y \in [(i-1)\Delta, i\Delta]} \lambda_o(\underline{x})(1-g(\underline{x})) I(x-\alpha_i^L)(\alpha_i^T - x).$$

indicate that the integrand depends on the y coordinate via $\lambda$ and g, which is independent of the parameters $\{\alpha_i^L, \alpha_i^T\}$. This observation allows one to first integrate along the y-direction, and reduces the problem to a 1-dimensional optimization. More specifically, for each leaf track i, one can define the corresponding 1D function $$c_{i,u}(x) = \int_{(i-1)\Delta}^{i\Delta} \lambda_u(\underline{x}) g(\underline{x}) dy$$

$$c_{i,o}(x) = \int_{(i-1)\Delta}^{i\Delta} \lambda_o(\underline{x})(1-g(\underline{x})) dy.$$

These definitions reduce the cost function to $$\Phi_{u,i} = \int c_{i,u}(x)[(I(\alpha_i^L - x) + I(x - \alpha_i^T)] dx$$

$$\Phi_{o,i} = \int c_{i,o}(x) I(x-\alpha_i^L) I(\alpha_i^T - x).$$

It can be shown with simple arithmetic manipulation that minimizing $\Phi_i$ is equivalent to minimizing $$\Psi_i = \int_{\alpha_i^L}^{\alpha_i^T} [-c_{i,u}(x) + c_{i,o}(x)] dx.$$

Let $$c_i \triangleq (c_{i,u} + c_{i,o}),$$

then the first order necessary condition for optimality is given by $$\frac{\partial}{\partial \alpha_i^L} \Psi_i \bigg|_{\alpha_i^L = x} = c_i(x) = 0;$$

$$\frac{\partial}{\partial \alpha_i^T} \Psi_i \bigg|_{\alpha_i^T = x} = -c_i(x)(x) = 0.$$

In addition, $\Phi_i$ needs to be locally convex at the optimal $\{\alpha_i^L, \alpha_i^T\}$. Fortunately, the leading and trailing leaf positions are only related by the constraint that $(\alpha_i^L < \alpha_i^T)$, and otherwise decoupled. This implies a diagonal Hessian matrix when $\Phi_i$ is twice differentiable, and the positive-definiteness of the Hessian reduces to the positiveness of the diagonal elements $$\frac{\partial^2}{\partial (\alpha_i^L)^2} \Psi_i > 0;$$

$$\frac{\partial^2}{\partial (\alpha_i^T)^2} \Psi_i > 0.$$

Substituting the expressions from $$\frac{\partial}{\partial \alpha_i^L} \Psi_i \bigg|_{\alpha_i^L = x} = c_i(x) = 0;$$

$$\frac{\partial}{\partial \alpha_i^T} \Psi_i \bigg|_{\alpha_i^T = x} = -c_i(x)(x) = 0.,$$

the second order condition reads $$\frac{\partial^2}{\partial (\alpha_i^L)^2} \Psi_i \bigg|_{\alpha_i^L = x} = c_i'(x) > 0;$$

$$\frac{\partial^2}{\partial (\alpha_i^T)^2} \Psi_i \bigg|_{\alpha_i^T = x} = -c_i'(x) > 0.$$

These analyses induce some observations for the behavior of the 1D function $c_i$ which are interpreted as the competing strength of local underdose and overdose cost. These observations include:

Both $\alpha_i^L$ and $\alpha_i^T$ fall on the zero-crossings of $c_i$.

$c_i$ moves upwards at $\alpha_i^L$, indicating that underdose cost starts to dominate overdose at the leading leaf position. This is expected as the transition from the normal tissue region to the target region occurs.

$c_i$ moves downwards at $\alpha_i^T$, indicating that overdose cost starts to dominate underdose at the trailing leaf position. This marks the transition from the target region to the normal tissue region along the leaf track.

A general observation from combining the above is that tumors with large local underdose cost drive the aperture open to ensure its coverage, and normal tissue regions with high overdose cost shall be shielded with the leaves.

A similar perturbation principle applies to cases when c is nondifferentiable, and yields the following results:

$$c(\alpha_i^L-) < 0, \; c(\alpha_i^L+) > 0;$$

$$c(\alpha_i^T-) > 0, \; c(\alpha_i^T+) < 0,$$

where − and + indicate a small perturbation in the negative and positive directions respectively. The zero-crossing conditions are implied by the continuity of the function c and thus dropped for simplicity. A semi-exhaustive algorithm for general inhomogeneous cost is presented in Algorithm 1 below:

---
Algorithm 1 Semi-exhaustive leaf sequencing
algorithm for general inhomogeneous cost
---

```
for i = 1 to N do
    Compute 1D functions c_{i,u}, c_{i,o} (4) and c_i = c_{i,u} − c_{i,o}.
    Find set C_i^L = {x : I(c(x + δ))I(−c(x − δ)) = 1}.
    Find set C_i^T = {x : I(c(x − δ))I(−c(x + δ)) = 1}.
    Initialize α̂_i^L = 0, α̂_i^T = 0; Φ̂_i = Φ_i(α̂_i^L, α̂_i^T).
    for α_i^L ∈ C_i^L do
        for α_i^T ∈ C_i^T and α_i^T > α_i^L do
            Φ̃_i = Φ_i(α_i^L, α_i^T).
            if Φ̃_i < Φ̂_i then
                α̂_i^L = α_i^L,  α̂_i^T = α_i^T ; Φ̂_i = Φ̃_i.
            end if
        end for
    end for
end for
{α̂_i^L, α̂_i^T}_{i=1}^N provides optimal leaf positions.
```

As a special case, homogeneous unitary underdose and overdose cost may be assigned across the ROI. This occurs when insufficient structural information can be used for a localized assignment. The homogeneous assumption, $\lambda u(\underline{x}) = \lambda u$ and $\lambda o(\underline{x}) = \lambda o$, can be used to further reduce the complexity of the general algorithm by pulling the constants out of the integrations, resulting in Algorithm 2 below:

---
Algorithm 2 Semi-exhaustive leaf sequencing
algorithm for homogeneous unitary cost
---

```
Compute κ = λ_u/(λ_o + λ_u).
for i = 1 to N do
    Compute 1D functions l_i(x) = ∫_{(i−1)Δ}^{iΔ} g(x)dy.
    C_i = {x : l_i(x) = κΔ}.
    Initialize α̂_i^L = 0, α̂_i^T = 0; Φ̂_i = Φ_i(α̂_i^L, α̂_i^T).
    for α_i^L ∈ C_i do
        for α_i^T ∈ C_i and α_i^T > α_i^L do
            Φ̃_i = Φ_i(α_i^L, α_i^T).
            if Φ̃_i < Φ̂_i then
                α̂_i^L = α_i^L,  α̂_i^T = α_i^T ; Φ̂_i = Φ̃_i.
            end if
        end for
    end for
end for
{α̂_i^L, α̂_i^T}_{i=1}^N provides optimal leaf positions.
```

To demonstrate the behavior of the optimization method according to the current invention, two illustrative examples are presented, one that demonstrates the effect of inhomogeneous underdose and overdose cost on leaf sequencing; and another presents the adaptation of an IMRT plan when the ROI undergoes rotational motion.

In this first example, the behavior of the leaf sequencing method is demonstrated in the presence of differential motion between tumor target and surrounding critical structures. An anatomy having a spherical tumor target and an arc-shaped critical structure is simulated. A reference plan is generated when the tumor target is relatively far from the critical structure. Inhomogeneous underdose and overdose unitary cost is assigned according to the discussion above, with a high overdose cost assigned to the critical structure.

During the simulated treatment process, when the tumour target approaches the critical structure, both the reference plan and the monitored tumour target motion are streamlined into the leaf sequencing algorithm. At each time instant, the ideal aperture is generated as the composition of the initial plan with the target motion. FIGS. 3a-3d show snapshots of the evolution of a simulated anatomy 300 having a tumor 302, and automatically generated leaf patterns 304 for a case with a high critical structure 306 overdose cost. This example mimics the differential motion between lung tumors and the adjacent spinal cord.

Figure 4:
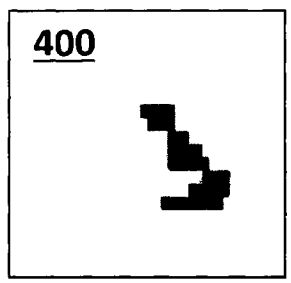
FIGS. 4a-4h show an original and undeliverable IMRT field and the deliverable beam under various overdose/underdose tradeoff configurations, according to the current invention.
Figure 4:
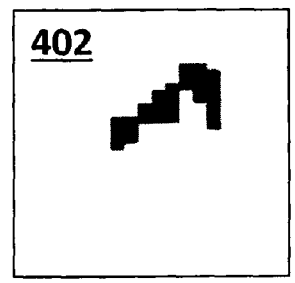
Figure 4:
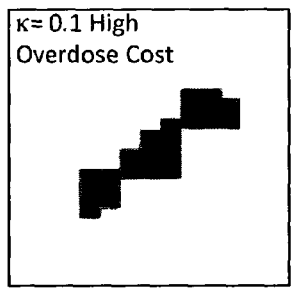
Figure 4:
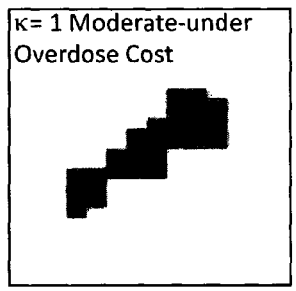
Figure 4:
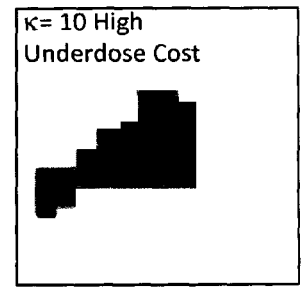
Figure 4:
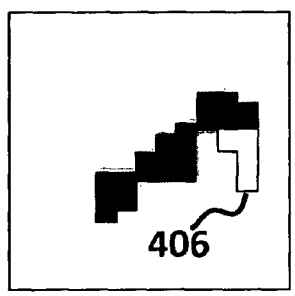
Figure 4:
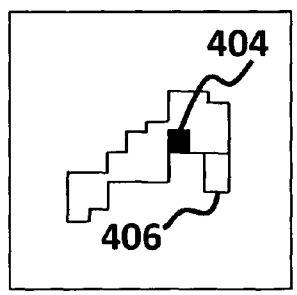
Figure 4:
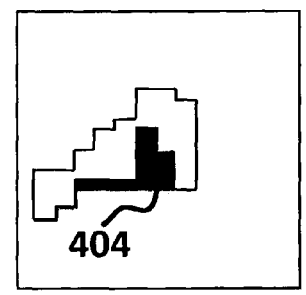

Rotations exceeding 45 degrees for lung tumors and 30 degrees for prostate tumors severely compromise dose delivery. When IMRT treatment is adapted to ROI rotations of such magnitude, the composite ideal aperture is highly likely to be nonconvex along certain leaf tracks, making the beam pattern undeliverable and necessitates a tradeoff between tumor underdose and normal tissue exposure. To illustrate this scenario, assume the only input to the tracking system is the planned IMRT aperture and global rotational information, which can be obtained from electromagnetic tracking or real-time imaging. FIGS. 4a-4b shows the original IMRT plan aperture 400 and an ideal aperture shape 402 corresponding to 90 degree rotation, where the choice of 90 degree rotation angle is merely for the convenience of visualization. Since the rotated aperture 402 shape cannot be delivered by the MLC, various underdose/overdose tradeoff results in different aperture patterns that are deliverable. The parameter $\kappa=\lambda o/(\lambda o+\lambda u)$ describes such a tradeoff. As the unitary underdose cost increases relative to the overdose cost, the optimal aperture pattern tends to be more tolerant towards overdosing the normal regions to ensure target coverage. As shown, FIGS. 4c-4e are the optimal deliverable apertures with corresponding κ parameter, and FIGS. 4f-4h are the optimal deliverable aperture overlays with the ideal rotated apertures. Further shown are the corresponding overdose 404 and underdose 406 regions.

The optimization principles of the current invention provide a systematic method to understand and make explicit decisions about the tradeoffs between tumor underdose and normal tissue overdose, when the ideal beam pattern is undeliverable. When the ideal pattern is deliverable, the solution to the optimization problem coincides with it regardless of the specific assignment of tradeoff.

The objective function value corresponding to the optimal solution indicates the minimal amount of delivery discrepancy using the MLC. Therefore, this value can be used to determine whether to pause the treatment beam to trade efficiency for higher dose conformality. By the same token, the optimization principle of the current invention can be naturally extended to incorporate other levels of tradeoff and result in a benign hybrid optimization problem. Additional physical considerations such as limited leaf velocity can be naturally incorporated into the invention by modifying the optimization setup with proper constraints. In principle, the underdose/overdose unitary cost needs to be assigned based on tissue property (tumor vs. normal tissue, parallel or serial, radiosensitivity, etc). In practice, such information is often known approximately. Despite this uncertainty, assigning inhomogeneous underdose and overdose unitary costs guides the sequencing algorithm towards a leaf configuration that offers improved tumor coverage and normal tissue protection. Accumulative dose discrepancy may also be incorporated by assigning a higher underdose unitary cost to voxels that have received lower dose than desired up to the time point of consideration, and conversely assigning a higher overdose unitary cost to voxels that are already overdosed. This mechanism would have a negative feedback feature to potentially prevent systematic underdose and/or overdose.

The current invention includes adapting an optimized plan aperture to the instantaneous motion. This setup alleviates the burden of MLC modeling such as accounting for the tongue and grove effect, as they are implicitly incorporated in the treatment planning process. Similarly, starting from a treatment plan also relieves one of the task of sequencing MLC leaves and optimizing their velocities to achieve a desired intensity modulation, and allows one to focus on investigating the adaptation of an aperture under deformation.

Two components contribute to the overall computation complexity of the proposed algorithm: (1) the numerical integration to yield $c_i$ (or $l_i$ in the homogeneous cost case) and (2) the search routine for the optimal placement. For the general inhomogeneous case, the numerical integration has a complexity proportional to the computation resolution in the BEV (Nx×Ny), where Nx and Ny are the discretization levels along and perpendicular to the leaf track respectively. The semi-exhaustive search scheme for optimal leaf placement has a complexity of $\sim O(N_x^2)$. With the relatively thin leaves and the overdose and underdose cost to be reasonably smooth, it is often the case that Ny<<Nx and the overall computation is dominated by $\sim O(N_x^2)$. Homogeneity of the unitary overdose/underdose cost and/or other structural assumptions (such as local convexity of the aperture), when utilized wisely, may further reduce the computation complexity.

In summary, the current invention is a new optimization-based leaf adaptation methodology that explicitly penalizes underdose/overdose error. This method is generally applicable to all types of geometrical and topological changes of the anatomy, as well as various plan types.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example it is applicable when the initial plan is optimized with respect to a MLC geometry set that is different from the delivery MLC, (e.g., superresolution plan or conventional plan to be delivered with a finer MLC). Tongue and groove effect as well as delivery leakage can be naturally incorporated via substituting the indicator functions described above to more specific leaf geometry descriptors.

All such variations are considered to be within the scope and spirit of the present invention as defined by the following claims and their legal equivalents.

What is claimed:

1. A method of multileaf collimator (MLC) leaf positioning in tracking-based adaptive radiotherapy, comprising:
    a. determining a radiotherapy beam pattern in real-time during a radiotherapy treatment beam delivery, wherein said radiotherapy beam pattern comprises transforming a treatment beam plan into radiotherapy beam coordinates;
    b. determining a dose discrepancy between said radiotherapy beam pattern and a deliverable MLC aperture in said real-time during said radiotherapy treatment beam delivery, wherein said dose discrepancy comprises a sum of an overdose cost and an underdose cost to a treatment volume;
    c minimizing said dose discrepancy in said real-time during said radiotherapy treatment beam delivery according to instantaneous target motion, wherein said dose discrepancy minimization provides a determined deliverable MLC aperture for said radiotherapy beam that configures said multileaf aperture to shape a radiotherapy beam that optimally accounts for changes in a patient's anatomy measured during said radiotherapy treatment beam delivery; and d. collapsing a plan aperture f and an estimated anatomical motion T onto a beam-eye-view plane, wherein an ideal motion-compensated aperture is determined by composing said plane aperture f with said collapsed beam-eye-motion plane according to g=f∘T, wherein said map is represented with a binary function over a region of interest (ROI), wherein said ROI: $\Omega \rightarrow \{0,1\}$ so that $$g(x) = \begin{cases} 1 & x \in \text{transformed plan aperture opening,} \\ 0 & \text{else,} \end{cases}$$

wherein x=(x, y) denotes a beam element location in said BEV.

2. The method of claim 1, wherein said radiotherapy beam coordinates are based on a projection of i) a translation of at least part of said radiotherapy beam pattern, ii) a rotation of at least part of said radiotherapy beam pattern, and iii) a deformation of at least part of said radiotherapy beam pattern, or i), ii) or iii).

3. The method of claim 1, wherein said overdose cost comprises an integration of pixelwise overdose penalties, wherein said overdose penalties can be spatially variant.

4. The method of claim 1, wherein said underdose cost comprises an integration of pixelwise underdose penalties, wherein said underdose penalties can be spatially variant.

5. The method of claim 1, wherein at least one previously determined said dose discrepancy is used when determining a next said deliverable MLC aperture for said radiotherapy beam.

6. The method of claim 1, wherein a determination of said overdose cost and a determination of said underdose cost are based on a tissue type and a radio-sensitivity of said tissue.

* * * * *